United States Patent
Tisato et al.

(10) Patent No.: US 8,182,789 B2
(45) Date of Patent: May 22, 2012

(54) INTERMEDIATE COMPOUND OF TECHNETIUM NITRIDE COMPLEX FOR RADIODIAGNOSTIC IMAGING

(75) Inventors: Francesco Tisato, Padua (IT); Fiorenzo Refosco, Valdagno (IT); Cristina Bolzati, Mirabello (IT); Stefania Agostini, Carzano (IT); Marina Porchia, Padua (IT); Mario Cavazza-Ceccato, Montecchio Maggiore (IT); Shinji Tokunaga, Chiba (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 955 days.

(21) Appl. No.: 12/160,920

(22) PCT Filed: Jan. 20, 2006

(86) PCT No.: PCT/JP2006/301260
§ 371 (c)(1),
(2), (4) Date: Jul. 15, 2008

(87) PCT Pub. No.: WO2007/083395
PCT Pub. Date: Jul. 26, 2007

(65) Prior Publication Data
US 2010/0160615 A1    Jun. 24, 2010

(51) Int. Cl.
*A61K 51/00* (2006.01)
*A61M 36/14* (2006.01)

(52) U.S. Cl. ............... 424/1.77; 424/1.11; 424/1.65; 568/8; 568/300

(58) Field of Classification Search .......... 424/1.11, 424/1.65, 1.77, 9.1, 9.3, 9.4, 9.5, 9.6, 9.7, 424/9.8; 568/8, 300; 534/7–14
See application file for complete search history.

(56) References Cited

U.S. PATENT DOCUMENTS

| | | | |
|---|---|---|---|
| 3,492,193 A | 1/1970 | Tesoro | |
| 3,711,577 A | 1/1973 | Maier | |
| 4,880,007 A | 11/1989 | Sadler et al. | |
| 5,288,476 A | 2/1994 | Pasqualini et al. | |
| 5,300,278 A | 4/1994 | Pasqualini et al. | |
| 5,399,339 A | 3/1995 | Pasqualini et al. | |
| 5,496,929 A | 3/1996 | Pasqualini et al. | |
| 6,270,745 B1 | 8/2001 | Duatti et al. | |
| 2004/0018147 A1 | 1/2004 | Duatti et al. | |

FOREIGN PATENT DOCUMENTS

| | | |
|---|---|---|
| CN | 1583770 A | 2/2005 |
| JP | 62-42934 A | 2/1987 |
| JP | 11-511041 A | 9/1999 |
| JP | 2004-505064 A | 2/2004 |
| WO | 89/08657 A2 | 9/1989 |
| WO | 90/06137 A1 | 6/1990 |
| WO | 92/00982 A1 | 1/1992 |
| WO | 93/01839 A1 | 2/1993 |
| WO | 96/39107 A1 | 12/1996 |
| WO | 98/27100 A1 | 6/1998 |

OTHER PUBLICATIONS

Boschi et al (Bioconjugate Chemistry, 2001, vol. 12, No. 6, pp. 1035-1042).*
Kim Young-Seung et al, "A Novel Ternary Ligand System Useful for Preparation of Cationic 99mTc-Diazenido Complexes and 99mTc-Labeling of Small Biomolecules," Bioconjugate Chemistry, vol. 17, No. 2, Jan. 17, 2006, pp. 473-484.
Official Action received from the Japanese Patent Office, in corresponding Japanese Patent Application No. JP2008-534589, mailed Nov. 15, 2011.

* cited by examiner

*Primary Examiner* — D L Jones
(74) *Attorney, Agent, or Firm* — Sughrue Mion, PLLC

(57) ABSTRACT

A bisphosphonoamine compound represented by the following formula (I): wherein R1, R2, R3, R4 and R5 are independently an alkyl group having 1 to 6 carbon atoms, and n is an integer of 1 to 6, is extremely useful as an intermediate for preparing a technetium nitride complex for radiodiagnostic imaging.

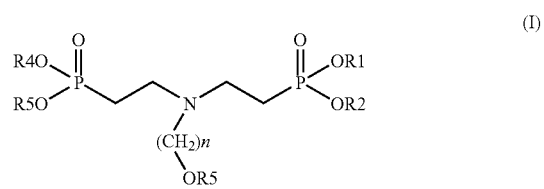

(I)

5 Claims, No Drawings

INTERMEDIATE COMPOUND OF TECHNETIUM NITRIDE COMPLEX FOR RADIODIAGNOSTIC IMAGING

TECHNICAL FIELD

The present invention relates to an intermediate compound of a technetium nitride complex used for radiodiagnostic imaging. More specifically, the present invention relates to an intermediate compound, namely a bisphosphonoamine compound, for preparing a technetium nitride complex used for radiodiagnostic imaging, a method for preparing the intermediate compound, a method for preparing the technetium nitride complex using the intermediate compound, and also to a radiopharmaceutical composition containing as an active ingredient the technetium nitride complex prepared by the above method.

BACKGROUND ART

Among radioactive transition metals used in radiopharmaceuticals, Tc-99m is a nuclide most often used in the field of radiodiagnostic imaging because it is advantageous, for example, in that, since the energy of γ-rays emitted by Tc-99m is 141 keV and the half-life of Tc-99m is 6 hours, Tc-99m is suitable for imaging, and that Tc-99m can easily be obtained by means of a $^{99}$Mo-$^{99m}$Tc generator. Thus, if a physiologically active substance can be attached to this nuclide without impairing the activity, the resulting compound is considered to be useful as a diagnostic agent.

The various attempts have been made to achieve such attachment, as described below. Transition metal nitride complexes are excellent in stability to hydrolysis. Therefore, when a transition metal nitride complex is subjected to exchange reaction with any of various ligands having a physiological activity, the nitride group of the nitride complex can remain bonded strongly to the metal atom. Accordingly, technetium nitride complexes having various substituents have been proposed. For example, WO 90/06137 discloses diethyl bisdithiocarbamate-Tc nitride complex, dimethyl bisdithiocarbamate-Tc nitride complex, di-n-propyl bisdithiocarbamate-Tc nitride complex and N-ethyl-N-(2-ethoxyethyl) bisdithiocarbamate-Tc nitride complex. Further, WO 89/08657, WO 92/00982 and WO 93/01839 disclose processes for producing a technetium nitride complex which comprises the steps of reacting a polyphosphine as a reducing agent for technetium with technetium oxide, reacting a nitride of a metal or ammonium as a nitrogen source for nitride with the reaction product to convert it to the corresponding nitride, and coordinating a physiologically active monoclonal antibody with this nitride.

In these processes, the choice of the physiologically active ligand is so important that it determines properties of the resulting pharmaceutical. Nevertheless, the metal nitride complex can have various numbers of coordination positions from monodentate to tetradentate and hence is formed in plural forms. Therefore, it has been difficult to obtain a single complex stoichiometrically having a specific physiologically active ligand.

WO 98/27100 discloses that, when a bisphosphine compound is coordinated at two of the four coordination positions of technetium-99m nitride and a bidentate ligand having an electron-donating atom pair is coordinated at the remaining two coordination positions, the bidentate ligand is stoichiometrically coordinated, so that a single technetium-99m nitride heterocomplex can be stably obtained.

JP 2004-505064 A describes a technetium-99m nitride complex wherein a bisphosphine compound is coordinated at two of the four coordination positions thereof and a specific bidentate ligand is coordinated at the remaining two coordination positions thereof. Further, JP 2004-505064 A describes that the technetium-99m nitride complex is markedly accumulated in specific organs such as heart and adrenal glands, and hence is useful for radiodiagnostic imaging. However, it is extremely complicated and difficult to prepare the bisphosphine compound which is an intermediate for preparing the technetium-99m nitride complex.

DISCLOSURE OF INVENTION

In view of such situations, the present invention is intended to provide an intermediate compound useful for effectively preparing a technetium nitride complex which is markedly accumulated in specific organs such as heart and adrenal glands and hence is extremely useful for radiodiagnostic imaging.

Thus, the present invention relates to a bisphosphonoamine compound represented by the following formula (I):

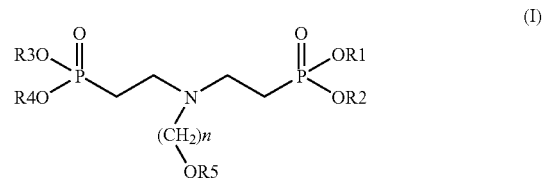

wherein R1, R2, R3, R4 and R5 are independently an alkyl group having 1 to 6 carbon atoms, and n is an integer of 1 to 6.

Further, the present invention relates to a method for preparing a bisphosphonoamine compound represented by the formula (I), which comprises the step of:

reacting a vinylphosphono compound of the following formula (II):

wherein R1 and R2 are as defined above, with a phosphonoamine compound of the following formula (III):

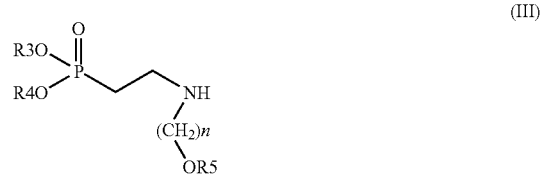

wherein R3, R4, R5 and n are as defined above, in the presence of a condensation reaction catalyst.

Further, the present invention relates to a method for preparing a bisphosphinoamine compound of the following formula (IV):

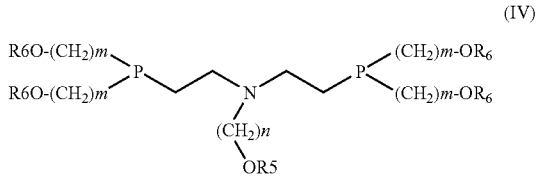

(IV)

wherein R5 and n are as defined above, R6 is an alkyl group having 1 to 6 carbon atoms, and m is an integer of 1 to 6, which comprises the steps of:

reducing a bisphosphonoamine compound represented by the formula (I) with a reducing agent to produce a bisphosphinoamine compound of the following formula (V)

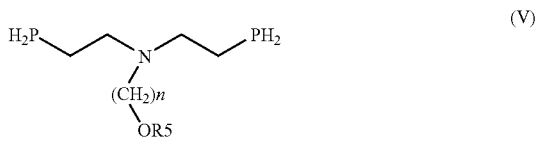

(V)

wherein R5 and n are as defined above, and reacting the compound of the formula (V) with a halogenated compound of the following formula (VI):

$$X—(CH_2)_m—OR6 \quad (VI)$$

wherein X is a halogen atom, and R6 and m are as defined above.

Further, the present invention relates to a method for preparing a technetium nitride complex of the following formula (VII):

$$[^{99m}Tc(N)(PNP)(DTC)]^+ \quad (VII)$$

wherein PNP is a bisphosphinoamine compound of the formula (IV), and DTC is a dithiocarbamate, which comprises the steps of:

conducting a method as mentioned above to produce the bisphosphinoamine of the formula (IV), reacting the bisphosphinoamine compound of the formula (IV) and the dithiocarbamate with a technetium oxide in the presence of a nitrogen donor.

Further, the present invention relates to a radiopharmaceutical composition for diagnostic imaging comprising as an active ingredient a technetium nitride complex prepared by a method as mentioned above.

BEST MODE FOR CARRYING OUT THE INVENTION

The bisphosphonoamine compound of the formula (I) is an intermediate extremely useful for preparing the bisphosphinoamine compound of the formula (IV) which is further used for finally preparing the technetium nitride complex of the formula (VII) useful for radiodiagnostic imaging.

In the bisphosphonoamine compound of the formula (I), R1, R2, R3, R4 and R5 are independently an alkyl group having 1 to 6 carbon atoms, and n is an integer of 1 to 6. Preferably, R1, R2, R3 and R4 are the same as each other. Such an alkyl group includes methyl, ethyl, n-propyl, iso-propyl, n-butyl, iso-butyl, n-pentyl and n-hexyl, and preferably includes methyl, ethyl, n-propyl or iso-propyl.

Preferred bisphosphonoamine compound of the formula (I) includes the following:

N,N-bis[(dimethyl 2-phosphono)ethyl]methoxyethylamine;
N,N-bis[(dimethyl 2-phosphono)ethyl]methoxypropylamine;
N,N-bis[(dimethyl 2-phosphono)ethyl]ethoxyethylamine;
N,N-bis[(dimethyl 2-phosphono)ethyl]ethoxypropylamine;
N,N-bis[(dimethyl 2-phosphono)ethyl]n-propoxyethylamine;
N,N-bis[(dimethyl 2-phosphono)ethyl]n-propoxypropylamine;
N,N-bis[(dimethyl 2-phosphono)ethyl]iso-propoxyethylamine;
N,N-bis[(dimethyl 2-phosphono)ethyl]iso-propoxypropylamine;
N,N-bis[(diethyl 2-phosphono)ethyl]methoxyethylamine;
N,N-bis[(diethyl 2-phosphono)ethyl]methoxypropylamine;
N,N-bis[(diethyl 2-phosphono)ethyl]ethoxyethylamine;
N,N-bis[(diethyl 2-phosphono)ethyl]ethoxypropylamine;
N,N-bis[(diethyl 2-phosphono)ethyl]n-propoxyethylamine;
N,N-bis[(diethyl 2-phosphono)ethyl]n-propoxypropylamine;
N,N-bis[(diethyl 2-phosphono)ethyl]iso-propoxyethylamine; and
N,N-bis[(diethyl 2-phosphono)ethyl]iso-propoxypropylamine.

The bisphosphonoamine compound of the formula (I) is prepared by reacting a vinylphosphono compound of the formula (II) with a phosphonoamine compound of the formula (III) in the presence of a condensation reaction catalyst, as shown on Reaction Scheme A below.

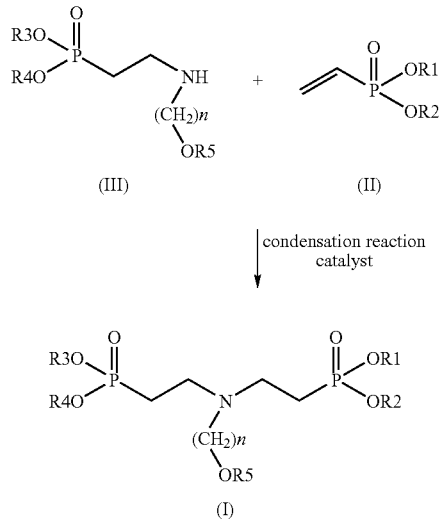

Reaction Scheme A

In the formulas (II) and (III), R1, R2, R3, R4, R5 and n are as defined above. The condensation reaction catalyst preferably includes lithium perchlorate. The reaction of the vinylphosphono compound of the formula (II) with the phosphonoamine compound of the formula (III) can be carried out by heating them in the presence of the condensation reaction catalyst in oil bath at a temperature of 60 to 80° C. for 5 to 10 hours. After the reaction, the resulting reaction product is extracted with an organic solvent such as trichloromethane, to yield the bisphosphonoamine compound of the formula (I).

The vinylphosphono compound of the formula (II) and the phosphonoamine compound of the formula (III) used in the Reaction Scheme A may be obtained according to a method of Reaction Scheme B below.

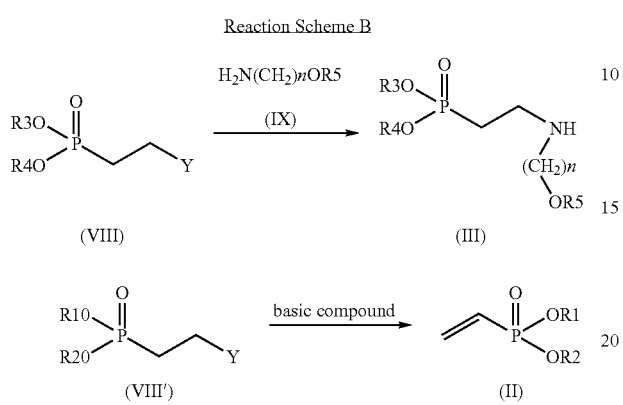

In the Reaction Scheme B, a halogenated compound of the formula (VIII) or (VIII'), wherein Y is a halogen atom such as bromine, fluorine, iodine or chlorine, is commercially available or may be readily prepared by known conventional methods. For instance, the halogenated compound may be prepared by reacting triethylphosphite with a dihalogenated ethane such as 1,2-dibromoethane and 1,2-dichloroethane at an excess amount at a temperature of 60 to 70° C. Also, an amine compound of the formula (IX) is commercially available or may be readily prepared by known conventional methods. The amine compound preferably includes 2-methoxyethlyamine, 2-ethoxyethylamine, 2-propanoxyethylamine, 2-isopropanoxyethylamine, 3-methoxyethylamine, 3-ethoxypropylamine, 3-propanoxypropylamine and 3-isopropanoxypropylamine. More preferably, the amine compound includes 2-methoxyethylamine and 2-ethoxyethylamine.

The halogen compound of the formula (VIII) is reacted with the amine compound of the formula (IX) in water at a temperature of 100 to 110° C. for 2 to 7 hours, followed by the treatment with a basic compound such as sodium hydroxide and potassium hydroxide, to produce the phosphonoamine compound of the formula (III). The halogenated compound of the formula (VIII') is heated in a solvent such as ethanol in the presence of a basic compound such as potassium hydroxide and sodium hydroxide at a temperature of 40 to 80° C. for 0.5 to 1 hour, to produce the vinyl compound of the formula (II).

Otherwise, as shown on Reaction Scheme C below, the halogenated compound of the formula (VIII) is reacted with the amine compound of the formula (IX) in the presence of potassium carbonate in an acetonitrile at a temperature of 60 to 70° C. for 2 to 3 hours to produce the phosphonoamine compound of the formula (III) together with the vinylphosphono compound of the formula (II'). Because R1, R2, R3 and R4 may be the same as each other as defined above, the vinylphosphono compounds of the formulas (II) and (II') may be also same as each other. Therefore, according to the Reaction Scheme C, the phosphonoamine compound of the formula (III) together with the vinylphosphono compound of the formula (II) may be conveniently prepared by a single reaction.

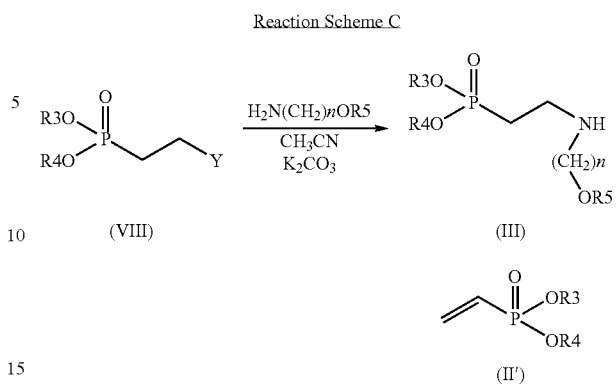

From the bisphosphonoamine compound of the formula (I) as the intermediate, a bisphosphinoamine compound of the formula (IV) can be prepared by a method as shown on Reaction Scheme D below.

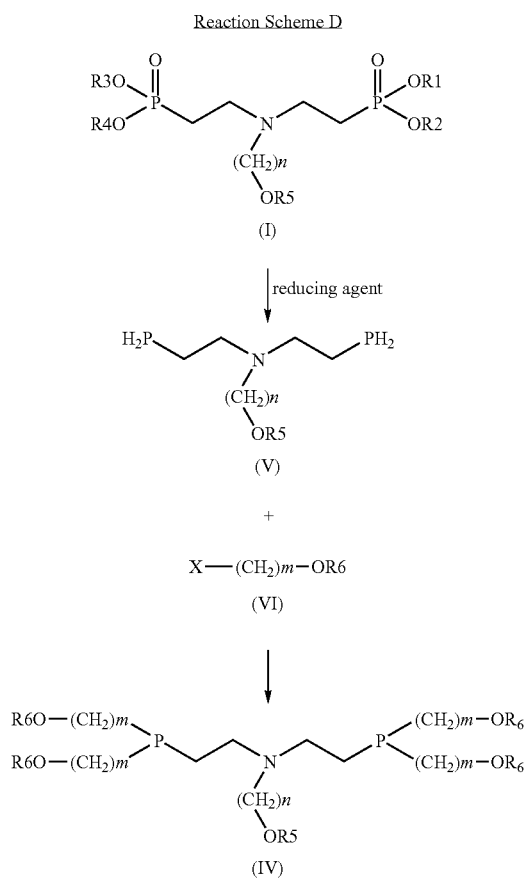

First, the bisphosphonoamine compound of the formula (I) is reduced with a reducing agent in an organic solvent to produce the bisphosphineamine compound of the formula (V). The reducing agent is preferably one having strong reducing activity. Such a reducing agent preferably includes aluminum lithium hydride and dichloroalane. The organic solvent preferably includes dry diethylether. The reduction of the bisphosphonoamine compound may carried out by reacting it with the reducing agent in the organic solvent at a temperature of −5 to 5° C. for 0.75 to 1 hours. The thus produced bisphosphineamine compound of the formula (V) preferably includes N,N-bis(2-phosphinoethyl)methoxyethylamine, N,N-bis(2-phosphinoethyl)ethoxyethylamine, N,N-bis(2-phosphinoethyl)methoxypropylamine and N,N-bis(2-phosphinoethyl)ethoxypropylamine.

Then, the thus produced bisphosphineamine compound of the formula (V) is reacted with a halogenated compound of the formula (VI) to produce the objective compound of the formula (IV). The halogenated compound of the formula (VI) preferably includes 1-methoxy-3-chloropropane, 1-ethoxy-3-chloropropane, 1-methoxy-2-chloroethane and 1-ethoxy-2-chloroethane.

The reaction of the bisphosphineamine compound with the halogenated compound can be carried out by first reacting the bisphosphineamine compound with an alkyl lithium such as n-butyllithium in an organic solvent such as dry tetrahydrofurane and then reacting the resulting reaction product with the halogenated compound at a temperature of −18 to 0° C. for 2 to 10 hours.

Thus, the objective bisphosphinoamine compound of the formula (IV) can be prepared.

Preferably, such a bisphosphinoamine compound includes the following:
Bis[(dimethoxyethylphosphino)ethyl]methoxyethylamine;
Bis[(dimethoxyethylphosphino)ethyl]methoxypropoxylamine;
Bis[(dimethoxyethylphosphino)ethyl]ethoxyethylamine;
Bis[(dimethoxyethylphosphino)ethyl]ethoxypropylamine;
Bis[(dimethoxyethylphosphino)ethyl]n-propoxyethylamine;
Bis[(dimethoxyethylphosphino)ethyl]n-propoxypropylamine;
Bis[(dimethoxyethylphosphino)ethyl]isopropoxyethylamine;
Bis[(dimethoxyethylphosphino)ethyl]isopropoxypropylamine;
Bis[(dimethoxypropylphosphino)ethyl]methoxyethylamine;
Bis[(dimethoxypropylphosphino)ethyl]methoxypropoxylamine;
Bis[(dimethoxypropylphosphino)ethyl]ethoxyethylamine;
Bis[(dimethoxypropylphosphino)ethyl]ethoxypropylamine;
Bis[(dimethoxypropylphosphino)ethyl]n-propoxyethylamine;
Bis[(dimethoxypropylphosphino)ethyl]n-propoxypropylamine;
Bis[(dimethoxypropylphosphino)ethyl]isopropoxyethylamine;
Bis[(dimethoxypropylphosphino)ethyl]isopropoxypropylamine;
Bis[(diethoxyethylphosphino)ethyl]methoxyethylamine;
Bis[(diethoxyethylphosphino)ethyl]methoxypropoxylamine;
Bis[(diethoxyethylphosphino)ethyl]ethoxyethylamine;
Bis[(diethoxyethylphosphino)ethyl]ethoxypropylamine;
Bis[(diethoxyethylphosphino)ethyl]n-propoxyethylamine;
Bis[(diethoxyethylphosphino)ethyl]n-propoxypropylamine;
Bis[(diethoxyethylphosphino)ethyl]isopropoxyethylamine;
Bis[(diethoxyethylphosphino)ethyl]isopropoxypropylamine;
Bis[(diethoxypropylphosphino)ethyl]methoxyethylamine;
Bis[(diethoxypropylphosphino)ethyl]methoxypropoxylamine;
Bis[(diethoxypropylphosphino)ethyl]ethoxyethylamine;
Bis[(diethoxypropylphosphino)ethyl]ethoxypropylamine;
Bis[(diethoxypropylphosphino)ethyl]n-propoxyethylamine;
Bis[(diethoxypropylphosphino)ethyl]n-propoxypropylamine;
Bis[(diethoxypropylphosphino)ethyl]isopropoxyethylamine;
Bis[(diethoxypropylphosphino)ethyl]isopropoxypropylamine;
Bis[(di-n-propoxyethylphosphino)ethyl]methoxyethylamine;
Bis[(di-n-propoxyethylphosphino)ethyl]met hoxypropoxylamine;
Bis[(di-n-propoxyethylphosphino)ethyl]ethoxyethylamine;
Bis[(di-n-propoxyethylphosphino)ethyl]ethoxypropylamine;
Bis[(di-n-propoxyethylphosphino)ethyl]n-propoxyethylamine;
Bis[(di-n-propoxyethylphosphino)ethyl]n-propoxypropylamine;
Bis[(di-n-propoxyethylphosphino)ethyl]isopropoxyethylamine;
Bis[(di-n-propoxyethylphosphino)ethyl]isopropoxypropylamine;
Bis[(di-n-propoxypropylphosphino)ethyl]methoxyethylamine;
Bis[(di-n-propoxypropylphosphino)ethyl]methoxypropoxylamine;
Bis[(di-n-propoxypropylphosphino)ethyl]ethoxyethylamine;
Bis[(di-n-propoxypropylphosphino)ethyl]ethoxypropylamine;
Bis[(di-n-propoxypropylphosphino)ethyl]n-propoxyethylamine;
Bis[(di-n-propoxypropylphosphino)ethyl]n-propoxypropylamine;
Bis[(di-n-propoxypropylphosphino)ethyl]isopropoxyethylamine;
Bis[(di-n-propoxypropylphosphino)ethyl]isopropanoxypropylamine;
Bis[(di-iso-propoxyethylphosphino)ethyl]methoxyethylamine;
Bis[(di-iso-propoxyethylphosphino)ethyl]methoxypropoxylamine;
Bis[(di-iso-propoxyethylphosphino)ethyl]ethoxyethylamine;
Bis[(di-iso-propoxyethylphosphino)ethyl]ethoxypropylamine;
Bis[(di-iso-propoxyethylphosphino)ethyl]n-propoxyethylamine;
Bis[(di-iso-propoxyethylphosphino)ethyl]n-propoxypropylamine;
Bis[(di-iso-propoxyethylphosphino)ethyl]isopropoxyethylamine;
Bis[(di-iso-propoxyethylphosphino)ethyl]isopropoxypropylamine;
Bis[(di-iso-propoxypropylphosphino)ethyl]methoxyethylamine;
Bis[(di-iso-propoxypropylphosphino)ethyl]methoxypropoxylamine;
Bis[(di-iso-propoxypropylphosphino)ethyl]ethoxyethylamine;
Bis[(di-iso-propoxypropylphosphino)ethyl]ethoxypropylamine;
Bis[(di-iso-propoxypropylphosphino)ethyl]n-propoxyethylamine;
Bis[(di-iso-propoxypropylphosphino)ethyl]n-propoxypropylamine
Bis[(di-iso-propoxypropylphosphino)ethyl]isopropoxyethylamine; and
Bis[(di-iso-propoxypropylphosphino)ethyl]isopropoxypropylamine;

More preferably, the bisphosphinoamine compound includes the following:
Bis[(dimethoxyethylphosphino)ethyl]methoxyethylamine;
Bis[(dimethoxyethylphosphino)ethyl]ethoxyethylamine;
Bis[(dimethoxypropylphosphino)ethyl]methoxyethylamine;
Bis[(dimethoxypropylphosphino)ethyl]ethoxyethylamine;
Bis[(diethoxyethylphosphino)ethyl]methoxyethylamine;
Bis[(diethoxyethylphosphino)ethyl]ethoxyethylamine;
Bis[(diethoxypropylphosphino)ethyl]methoxyethylamine; and
Bis[(diethoxypropylphosphino)ethyl]ethoxyethylamine.

Most preferably, the bisphosphinoamine compound includes the following:
Bis[(dimethoxyethylphosphino)ethyl]methoxyethylamine;
Bis[(dimethoxyethylphosphino)ethyl]Ethoxyethylamine;
Bis[(dimethoxypropilphosphino)ethyl]methoxyethylamine; and
Bis[(dimethoxypropylphosphino)ethyl]ethoxyethylamine.

By using the bisphosphinoamine compound of the formula (IV) as mentioned above, a technetium nitride complex can be prepared which is used for radiodiagnostic imaging. That is, a technetium nitride complex of the following formula (VII):

$$[^{99m}Tc(N)(PNP)(DTC)]^+ \qquad (VII)$$

wherein PNP is a bisphosphinoamine compound of the formula (IV), and DTC is a dithiocarbamate, can be prepared by reacting the bisphosphinoamine compound of the formula (IV) and the dithiocarbamate with a technetium oxide in the presence of a nitrogen donor.

The dithiocarbamate preferably includes pyrrolidine dithiocarbamate, piperidine dithiocarbamate, 4-ethyl-piperadine dithiocarbamate, N-diethoxyethyl dithiocarbamate, N-dimethyl dithiocarbamate, N-diethyl dithiocarbamate, N-dipropyl dithiocarbamate, N-methoxy-N-methyl dithiocarbamate, N-methoxyethyl-N-ethyl dithiocarbamate, N-methoxypropyl-N-ethyl dithiocarbamate, N-methoxyethyl-N-butyl dithiocarbamate, N-dimethoxyethyl dithiocarbamate, N-diethoxypropyl dithiocarbamate, N-diethoxybutyl dithiocarbamate, N-dipropoxyethyl dithiocarbamate, N-dibutoxyethyl dithiocarbamate, N-dimethoxypropyl dithiocarbamate, N-dimethoxyisopropyl dithiocarbamate, N-ethoxy-N-ethyl dithiocarbamate, N-ethoxypropyl-N-propyl dithiocarbamate, N-ethoxyethyl-N-isopropyl dithiocarbamate, N-methoxyethyl-N-isopropyl dithiocarbamate, N-ethoxyethyl-N-propyl dithiocarbamate, N-ethoxyethyl-N-ethyl dithiocarbamate and N-propoxy-N-ethyl dithiocarbamate. More preferably, the dithiocarbamate includes pyrrolidine dithiocarbamate, piperidine dithiocarbamate, 4-ethyl-piperadine dithiocarbamate, N-diethoxyethyl dithiocarbamate, N-dimethyl dithiocarbamate, N-diethyl dithiocarbamate, N-dipropyl dithiocarbamate, N-methoxy-N-methyl dithiocarbamate, N-ethoxy-N-ethyl dithiocarbamate, N-methoxyethyl-N-ethyl dithiocarbamate, N-ethoxyethyl-N-isopropyl dithiocarbamate, N-ethoxyethyl-N-ethyl dithiocarbamate, N-methoxypropyl-N-ethyl dithiocarbamate and N-dimethoxyethyl dithiocarbamate. Most preferably, the dithiocarbamate includes pyrrolidine dithiocarbamate, piperidine dithiocarbamate, 4-ethyl-piperadine dithiocarbamate, N-diethoxyethyl dithiocarbamate.

The nitrogen donor preferably includes dithiocarbazic acid, dithiocarbazic acid derivatives, hydrazine, hydrazine derivatives and hydrazide derivatives and phosphinoamines. Together with the nitrogen donor, a reducing agent may be used. Such a reducing agent preferably includes stannous chloride, sodium hydrogensulfite, sodium borohydride, tertiary phosphines and tris-(m-sulfonatophenyl)phosphine.

Specifically, the technetium nitride complex of the formula (VII) can be prepared as follows. First, a $^{99m}TcN$ intermediate is obtained by mixing the nitrogen donor, the reducing agent and Na[$^{99m}TcO_4$] as the technetium oxide eluted from a $^{99}Mo$—$^{99m}Tc$ generator. Then, the $^{99m}TcN$ intermediate is reacted with two different ligands, i.e., the bisphosphinoamine compound of PNP and a bidentate ligand of the dithiocarbamate, and preferably a solubilizer for PNP. Thus, the objective technetium nitride complex is obtained.

Otherwise, the technetium nitride complex of the formula (VII) can be readily prepared by using a kit containing the components necessary for forming the complex as mentioned above. For example, there are prepared a vial 1 containing the nitrogen donor, the reducing agent and preferably a stabilizer and a pH adjuster, and a vial 2 containing two different ligands, i.e., the bisphosphinoamine compound of PNP and a bidentate ligand of the dithiocarbamate, and a solvent for PNP. Then, Na[$^{99m}TcO_4$] as the technetium oxide eluted from a $^{99}Mo$—$^{99m}Tc$ generator is placed in the vial 1. On the other hand, physiological saline is placed in the vial 2 to dissolve the contents sufficiently, and a definite amount of the resulting solution is placed in the vial 1, followed by heating at about 100° C., whereby the technetium nitride complex can be obtained.

In the above methods, as the stabilizer, ethylenediaminetetraacetic acid (EDTA) is preferably used. As the pH adjuster, sodium phosphate buffer and sodium carbonate buffer are preferably used. Furthermore, for example, γ-cyclodextrin is preferably used as a surfactant to prevent attachment of the lipophilic technetium nitride complex to the rubber and syringe walls. Also, a solubilizer may be used for the bisphosphinoamine compound of PNP.

The thus obtained technetium nitride complex is markedly accumulated in heart and adrenal glands, and hence is extremely useful for diagnostic imaging of heart and adrenal glands.

The technetium nitride complex may be formulated into a radiopharmaceutical composition for diagnostic imaging by mixing under aseptic condition with pharmaceutically acceptable additives, for example, stabilizers such as ascorbic acid and p-aminobenzoic acid; pH adjusters such as sodium carbonate buffer and sodium phosphate buffet; solubilizers such as α,β,γ-cyclodextrins, meglumine; and excipients such as D-mannitol. The radiopharmaceutical composition for diagnostic imaging may be provided in the form of a kit for immediate preparation when used. Such a kit is obtained by combining the technetium nitride complex with the above additives.

The radiopharmaceutical composition may be administered by a conventional parenteral modes such as intravenous administration, and the dose thereof is determined depending on a radioactivity level at which imaging is considered possible, in view of the age and body weight of a patient, the condition of a disease to be cured, a radioactive imaging apparatus to be used, etc. The dose is usually 37 MBq to 1,850 MBq, preferably 185 MBq to 740 MBq, in terms of the radioactivity of technetium-99m.

The present invention is illustrated below in more detail with examples, but the present invention is not limited to those examples.

REFERENTIAL EXAMPLE 1

Synthesis of bis[(dimethoxypropylphosphino)ethyl]
ethoxyethylamine (PNP5) by a Known Method (i) Synthesis of 3-methoxy-1-propanol(1)

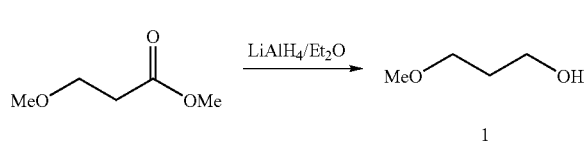

An oven dried 12 L flask was flushed with argon and charged with lithium aluminum hydride (78 g, 2.1 mol) and ether (3 L). Methyl-3-methoxypropionate (424 g, 3.59 mol) was added dropwise over a 4 hours period. After the addition was complete the mixture was stirred for an additional 30 minutes, then cooled to 0° C. The reaction was quenched by cautious dropwise addition of water (78 mL), followed by 15% sodium hydroxide (78 mL), and finally water (234 mL). Celite (200 g) was added as a filtering aid. The resulting mixture was stirred at room temperature for 30 minutes.

The brown suspension was filtered, and the filter cake was thoroughly washed with ether (500 mL). The combined filtrates were transferred to an extraction funnel. The aqueous phase was discarded, and the organic phase was drained into a 4 L Erlenmeyer flask. Anhydrous magnesium sulfate (100 g) was added to the flask and stirred for 30 minutes. The inorganic salt was filtered from the solvent solution, and the filtrate was concentrated on the rotary evaporator at atmospheric pressure to give 285 g clear colorless oil. The oil was stirred at room temperature under house vacuum overnight to give 196 g (60%) clear colorless oil. This intermediate was used in the next step without further purification.

(ii) Synthesis of 3-methoxy-1-chloropropane (2)

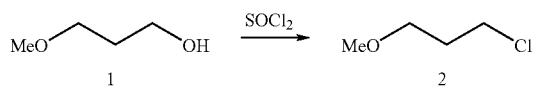

An oven dried 2 L flask was flushed with argon and charged with 3-methoxypropanol (1) (196 g, 2.17 mol) and anhydrous pyridine (176 mL, 2.17 mol). The flask was cooled to 10° C. in an ice water bath. Thionyl chloride (388 g, 3.26 mol) was added dropwise over a 4 hours period to ensure the temperature stayed between 10° C. and 30° C. After the addition was complete the mixture was heated to 70° C. for 4 hours, and then it was cooled to room temperature.

The crude reaction mixture was poured onto a slurry of ice (600 g) and concentrated hydrochloric acid (110 mL) with vigorous stirring. The biphasic solution was transferred to an extraction funnel. The organic phase was collected in a flask, and the aqueous phase was extracted with ether (300 mL). The combined organic phases were washed with 5% potassium carbonate (300 mL). The organic phase was dried over potassium carbonate (100 g). The organic phase was filtered, and the filtrate was concentrated on the rotary-evaporator to give 400 ml yellow liquid.

The crude product was distilled at atmospheric pressure at 105-108° C. to give 166.5 g (71%) clear colorless oil.

(iii) Synthesis of tetrakis(3-methoxypropyl)diphosphane disulfide (3)

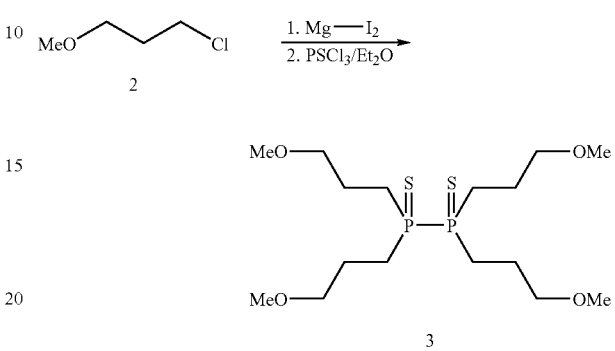

An oven dried 3 L flask was flushed with argon, and was charged with 3-methoxy-1-chloropropane (2) (66 g, 0.61 mol), magnesium turnings (37.2 g, 1.53 mol), and ether (1 L). The mixture was stirred for 10 minutes and then allowed to stand for 10 min. A single tiny crystal of iodine was dropped into the flask and positioned on the surface of a magnesium turning. Once the ether began to boil (approx. 15 min.) the remaining compound 2 (100 g, 0.92 mol) was added. The total amount of starting material was 166 g, 1.53 mol.

After the boiling stopped a solution of thiophosphoryl chloride (54 mL, 0.54 mol) in ether (363 mL) was prepared under argon and placed in an addition funnel. The Grignard reagent was cooled to 0° C., and the thiophosphoryl chloride solution was added dropwise to the reaction mixture over a 1 hour period while keeping the temperature between 0° C. and 5° C. After the addition was complete the reaction flask was allowed to warm to room temperature with continued stirring, and then the reaction was refluxed for 2 hours. Afterwards, it was cooled to 0° C.

The crude reaction mixture was poured into a slurry of ice (3.3 L) and sulfuric acid (134 mL) with vigorous stirring. The resulting biphasic solution was stirred at room temperature overnight. The solution was transferred by pressure to an extraction funnel in an argon atmosphere. The organic phase was collected and concentrated on the rotary evaporator to give 48 g (42%) clear colorless oil. This intermediate was used in the next step without purification.

(iv) Synthesis of bis(3-methoxypropyl)phosphine (4)

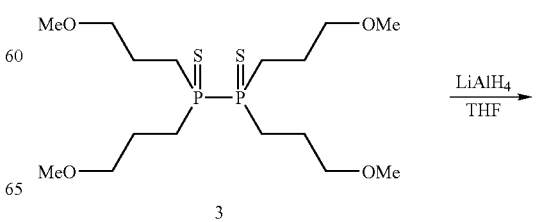

-continued

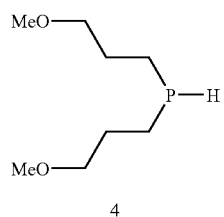

4

An oven dried 2 L flask was flushed with argon and charged with 1M lithium aluminum hydride in THF (168 mL, 168 mmol). Tetrakis(3-methoxypropane)diphosphane disulfide (3) (64 g, 153 mmol) was dissolved in degassed tetrahydrofuran (375 mL). This solution was added dropwise to the reaction flask over a 4 hours period with stirring. The solution was refluxed at 60° C. for 3 hours.

The reaction was cooled to 0° C. Cautiously, degassed water (6.4 mL) was added dropwise with vigorous stirring. Degassed 15% sodium hydroxide (6.4 mL) was added, and finally degassed water (19.2 mL) was added. Stirring was discontinued, and the mixture was allowed to stand at room temperature overnight under argon. Degassed ether (500 mL) and degassed water (500 mL) was added, and the mixture was stirred for 30 minutes. The stirring was stopped, and the phases were allowed to separate. The upper organic phase was transferred by pressure to a 3 L flask. The aqueous phase was extracted with ether (500 mL). The combined organic phases were dried over sodium sulfate (300 g) overnight. The dried organic phase was decanted by pressure into a 3 L flask using an in-line filter. The solution was concentrated under house vacuum with a dry ice/isopropanol filled condenser and minimal amount of heat.

The crude product was transferred by pressure to a 100 mL flask, and vacuum distilled (0.4 mm Hg) at 55° C.-60° C. to give 9.55 g (18%) clear colorless oil. This intermediate was used in the final step without any further purification.

(v) Synthesis of N-ethoxyethyl-N,N-diethanolamine (5)

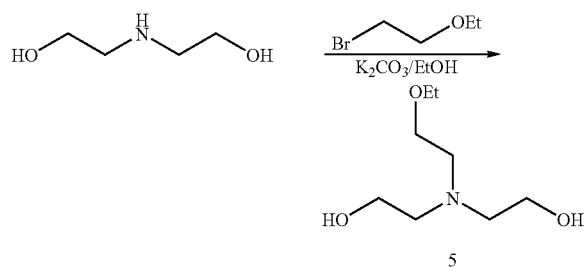

5

An oven dried 3 L flask was flushed with argon and charged with absolute ethanol (240 mL), potassium carbonate (276 g, 1.97 mol), and diethanolamine (120 mL, 1.14 mol). Bromoethyl ethyl ether (304 g, 1.97 mol) was added dropwise over a 3 hours period. The mixture was refluxed for 2 days under argon. The mixture was cooled to 0° C. and filtered. The filter cake was washed with ethanol (500 mL), and the combined filtrates were concentrated on the rotary evaporator to give 800 g yellow oil.

The crude product was vacuum distilled (0.5 mmHg) at 125°-127° C. to give 121 g (60%) light yellow oil. This intermediate was further purified silica gel (1 kg) using 10% methanol in dichloromethane (10 L) to give 60 g (30%) of the purified product.

(vi) Synthesis of N,N-bis(2-chloroethyl)-N-ethoxyethylamine (6)

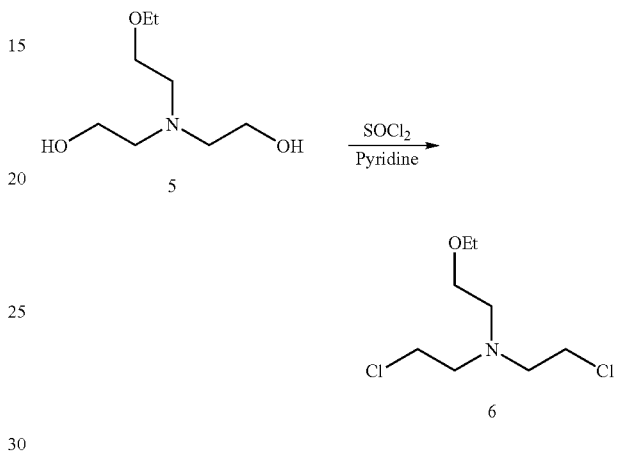

An oven dried 1 L flask was flushed with argon and charged with anhydrous pyridine (25 mL, 304 mmol), and N-ethoxyethyl-N,N-diethanolamine (5) (27 g, 152 mmol). The flask was cooled to 0° C. with a NaCl/ice water bath. Thionyl chloride (108.5 g, 912 mmol) was added dropwise over a 6 hour period while keeping the temperature between 0° C. and 10° C. The viscous reaction solution was stirred under argon at room temperature overnight in the absence of light.

The condenser was replaced with a distillation head, and the unreacted thionyl chloride was removed by vacuum distillation. The crude reaction mixture was cooled to 0° C. Cautiously, water (200 mL) was added dropwise to the flask with vigorous stirring. The mixture was stirred at 10° C. for 1 hour. The temperature was then decreased to −5° C. and sodium carbonate (40 g) was added portionwise with vigorous stirring. Stirring was continued for 1 hour while allowing the mixture reach room temperature. Ether (400 mL) was added, stirring was discontinued, and the phases were allowed to separate. The biphasic solution was transferred to an extraction funnel. The organic phase was set aside, and the aqueous phase was extracted with ether (200 mL). The combined organic phases were dried over magnesium sulfate (100 g), filtered, and the filtrate was concentrated on the rotary evaporator in the presence of toluene (20 mL) to give 37 g yellow oil.

The crude product was chromatographed on silica gel (400 g) using hexane/ether (5/1) [3 L]. The proper fractions were pooled and concentrated on the rotary evaporator. The purified product was stirred at room temperature overnight under house vacuum to give 19 g (58%) clear yellow oil. Storage of this intermediate over a three week period proved detrimental, and it had to be chromatographed a second time under similar conditions prior to its use in the final step. 7.

(vii) Synthesis of bis[(dimethoxypropylphosphino)ethyl]ethoxyethylamine (PNP5)

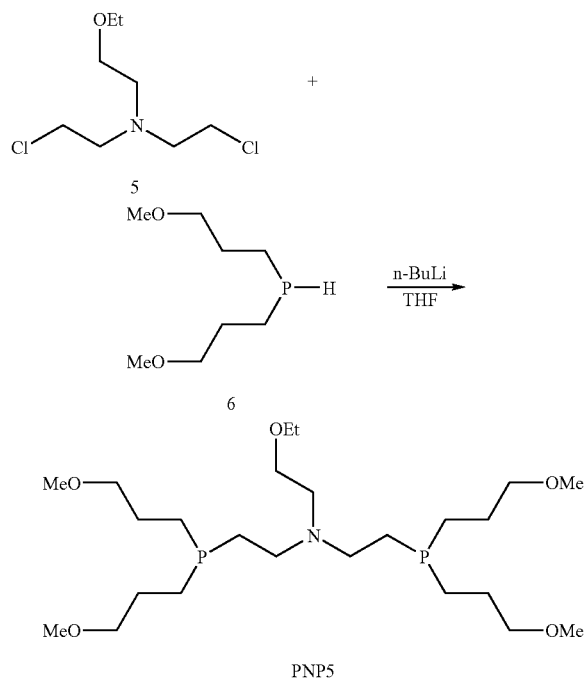

An oven dried 500 mL flask was flushed with argon and charged with bis(3-methoxypropyl)phosphine (4) (9.5 g, 53.3 mmol) and anhydrous THF (115 mL). n-Butyllithium (2.5 M in hexanes) [23.4 mL, 58.6 mmol] was added dropwise over a 4 hours period. The reaction flask was cooled to 0° C., and a solution containing N,N-bis(2-chloroethyl)-N-ethoxyethylamine (6) (5.7 g, 26.7 mmol) in anhydrous THF (10 mL) was added dropwise over a 3 hours period. The reaction was then stirred at room temperature overnight.

Cold degassed water (40 mL) was carefully added dropwise to the reaction flask. Degassed ether (100 mL) was added, and the biphasic solution was transferred by pressure to an extraction funnel. The aqueous layer was drained and set aside under argon. The organic phase was also drained and set aside under argon. The aqueous phase was extracted with degassed ether (30 mL). The combined organic phases were dried over sodium sulfate (20 g), filtered under an argon umbrella, and the filtrate was concentrated on the rotary-evaporator. The crude product was stirred under house vacuum overnight to give 12.17 g (92%) light yellow oil, which was 90% pure, by HPLC.

The crude product was chromatographed on silica (150 mL bed volume). The less polar impurities were washed off the column using hexane/ether (1/1) [2 L]. The desired product was eluted from the column with 5% methanol in dichloromethane. The proper fractions were pooled and concentrated to give 10 g (75%) light yellow oil, which was 94% pure, by HPLC. A second purification by silica gel chromatography similar to the first gave 6 g (45%) light yellow oil, which was 95.3% pure by HPLC. The purified product was stored under argon.

1H NMR (CDCl3): δ(ppm)=3.48 (m, 4H); 3.41 (t, 8H); 3.33 (s, 12H); 2.65 (m, 6H); 1.68 (m, 8H); 1.56 (m, 4H); 1.45 (m, 8H); 1.19 (m, 3H).

13C NMR (CDCl3): δ(ppm)=73.36 (d); 68.93 (s); 66.34 (s); 58.37 (s); 52.45 (s); 50.88 (d); 25.88 (d); 24.26 (d); 23.33 (d); 15.06 (s).

31P {1H} (CDCl3): δ(ppm)=−31.8.

As clear from the above Referential Example 1, the bisphosphinoamine compound was prepared by seven steps according to a known method as described in Claudio Bianchini et al., Organometallics 1995, 14, 1489-1502.

EXAMPLE 1

Synthesis of bis[(dimethoxypropylphosphino)ethyl]ethoxyethylamine (PNP5) by the method of the present invention

(i) Synthesis of diethyl (2-bromoethyl) phosphonate (1)

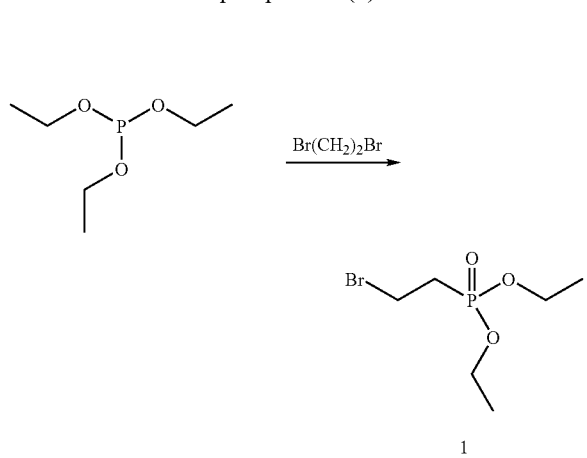

1,2-dibromoethane (69 ml, 0.8 mol) was poured into a two-necked 150 mL round-bottom flask. Triethylphosphite (34.3 ml, 0.2 mol) was added under stirring and the mixture was then refluxed for 2 hours. The excess of 1,2-dibromoethane was removed by rotary evaporation under gentle warming at 60-70° C. The residue was distilled under reduced pressure (2 mmHg, 95-105° C. or 1 mmHg, 75° C.). Yield 95%.

1H NMR (CDCl3), δ(ppm)=4.01 (m, 4H); 3.42 (q, 2H); 2.27 (m, 2H); 1.22 (t, 6H).

31P{1H} (CDCl3): δ(ppm)=26.4.

(ii) Synthesis of N,N-bis[(diethyl 2 phosphono)ethyl]ethoxyethylamine (4)

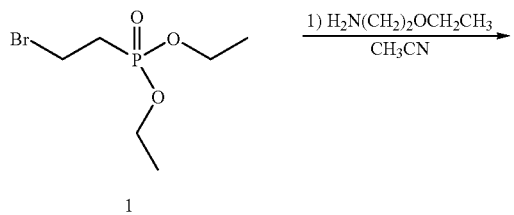

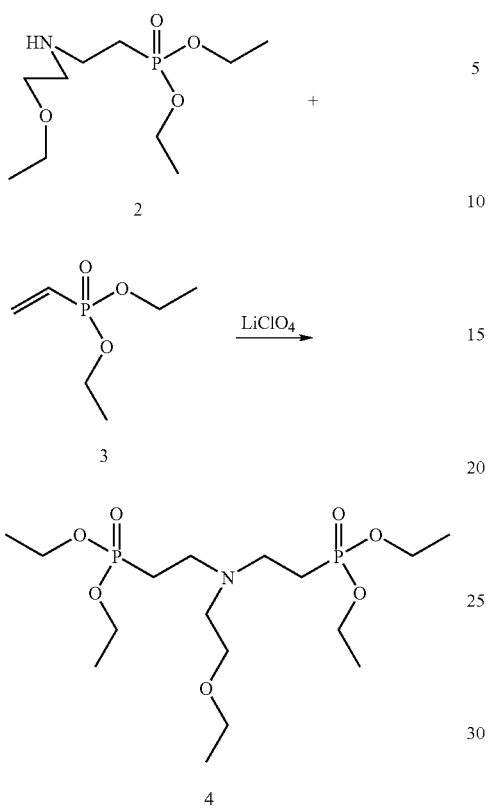

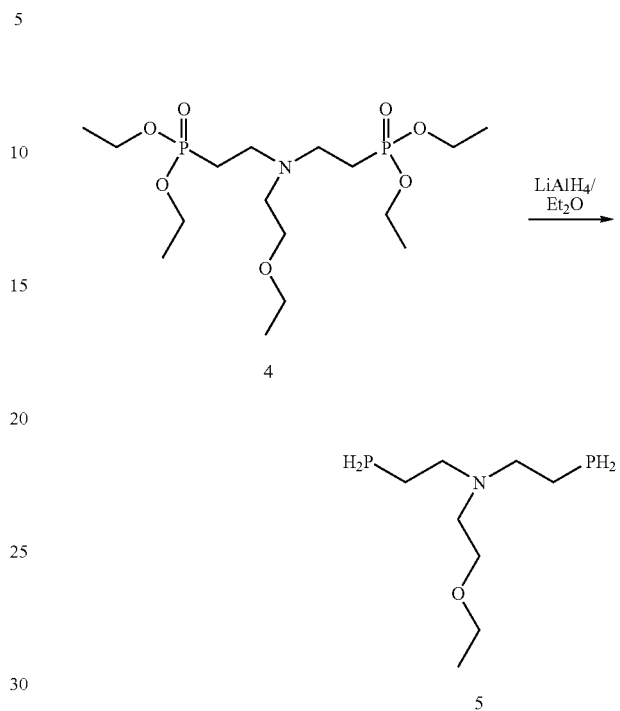

(iii) Synthesis N,N-bis(2-phosphinoethyl)ethoxyethylamine (5)

In a 50 mL two-necked round bottom flask equipped with an automatic stirrer and heater, and with a condenser, diethyl (2-bromoethyl)phosphonate (1) (0.45 ml, 2.5 mmol), 2-ethoxyethylamine (0.26 ml, 2.5 mmol), K2CO3 (0.346 g, 2.5 mmol) and acetonitrile (10 ml) were added. The mixture was maintained at 70° C. by means of an oil bath for 3 hours under stirring. After cooling the mixture was filtered (G3 frit), and washed with acetonitrile (2×3 ml). The solvent was totally removed by rotoevaporation giving a yellow oil. (31P{1H} NMR in CDCl3 showed two signals of ca. equal intensity at 31.2 and 18.0 ppm, corresponding to the monosubstituted intermediate 2 and a stoichiometric excess the vinyl derivative intermediate 3, respectively).

The yellow oil 0.70 ml recovered above was added to a 2 ml vial along with LiClO4 (133 mg, 1.25 mmol). The vial was degassed with dinitrogen, and then quickly and tightly closed. The vial was deepen for 7 hours at 75° C. in an oil bath. The resulting yellow oil was taken up with CHCl3 (3×2 ml), then was treated in a separator funnel with H2O (6 ml) and the lower organic layer was recovered. The water phase was treated again with CHCl3 (3 ml). The combined organic phases were finally concentrated with a dinitrogen stream and then under vacuum pump (to discharge the excess of unreacted 3). A viscous yellow oil was obtained (yield 85%).

1H NMR (CDCl3): $\delta$(ppm)=4.12-4.04 (m, 8H); 3.50-3.46 (m, 4H); 2.84-2.78 (m, 4H); 2.66-2.62 (t, 2H); 1.98-1.87 (m, 4H); 1.35-1.29 (t, 12H); 1.21-1.16 (t, 3H).

31P NMR (CDCl3): $\delta$(ppm)=31.3.

Freshly distilled anhydrous diethylether was added to a 100 ml two-necked round bottom flask containing N,N-bis[(diethyl 2-phosphono)ethyl]ethoxyethylamine (4) (533 mg, 1.28 mmol) under a dinitrogen atmosphere. The flask was cooled to 0° C. in an ice-bath. LiAlH4 (1.0 M in Et2O solution; 8 mL, 8 mmol) was added slowly (3 minutes) through a rubber septum with a syringe. Evolution of gaseous hydrogen was observed along with the characteristic smell of P(III). The ice bath was removed and the whitish cloudy mixture was left to stir at room temperature for 45 minutes. The flask was then cooled again to 0° C. (ice bath) and a degassed saturated water solution of Na2SO4 (5 ml) was added dropwise under dinitrogen (if necessary more diethylether may be added to maintain the volume of the reaction mixture constant). Under stirring, additional solid anhydrous Na2SO4 (300-500 mg) was added to the white Suspension to take off completely water. The mixture was then filtered off (G2 frit.) under a dinitrogen atmosphere and the filtrate was collected in a two-necked 50 mL flask. The solid on the frit was washed with diethylether (2×10 ml), and dichloromethane (2×10 ml). The combined organic phases were concentrated under a stream of dinitrogen, and then under vacuum (almost quantitative yield)

1H NMR (CDCl3): $\delta$(ppm)=3.50-3.48 (m, 4H); 2.95-2.90 (t, 2H); 2.68-2.66 (m, 6H); 2.30-2.25 (t, 2H); 1.64-1.62 (m, 4H); 1.29-1.17 (t, 3H).

31P{1H} (CDCl3): $\delta$(ppm)=−145.7.

(iv) Synthesis of bis[(dimethoxypropylphosphino)ethyl]ethoxyethylamine (PNP5)

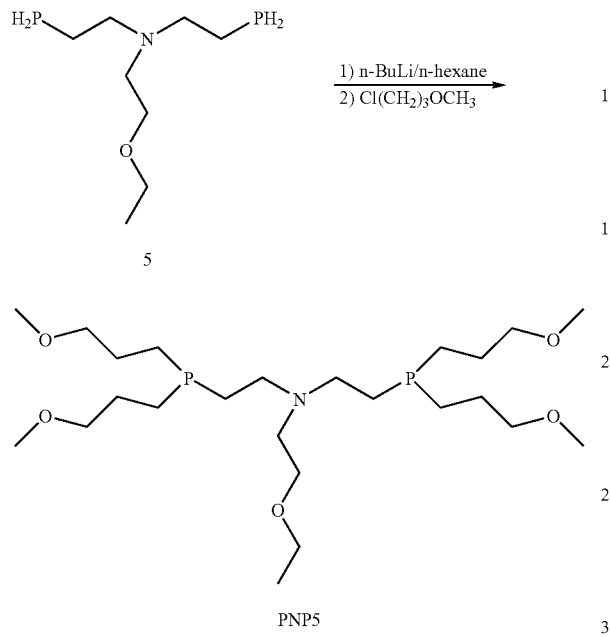

PNP5

A slight excess of n-BuLi (2.5 M in n-hexane; 2 mL, 4.87 mmol) was added via cannula under a dinitrogen atmosphere through a rubber septum to a flask containing N,N-bis(2-phosphinoethyl)ethoxyethylamine (5) (243 mg, 1.16 mmol) in freshly distilled THF (10 mL). The solution became pale yellow-green coloured. The flask was cooled to 0° C. with an ice bath and, under stirring, 1-methoxy-3-chloropropane (504 mg, 4.64 mmol) was added dropwise. The mixture was left to reach room temperature. The mixture was then reduced to one third of the initial volume by a gentle stream of dinitrogen. The flask was cooled again with an ice bath and degassed water (5 mL) was added dropwise. Two phases were formed. Diethylether (20 mL) is added and the mixture was transferred in a separatory funnel via cannula to avoid the contact with the atmosphere. Always under a dinitrogen atmosphere the lower aqueous phase was recovered in another separatory funnel and treated with additional diethylether (20 mL). Then the aqueous phase was discharged and the combined ethereal phases were placed in a 100 mL round bottom flask containing anhydrous Na2SO4 (500 mg). The solid was filtered off and washed with additional anhydrous diethylether (2×10 ml). The combined ethereal phases were concentrated under dinitrogen and then under vacuum (yield 58%).

1H NMR (CDCl3): δ(ppm)=3.55-3.44 (m, 4H); 3.42-3.38 (t, 8H); 3.32 (s, 12H); 2.68-2.61 (m, 6H); 1.75-1.63 (m, 8H); 1.59-1.56 (m, 4H); 1.48-1.42 (m, 8H); 1.22-1.17 (m, 3H).

13C NMR (CDCl3): δ(ppm)=73.57 (d); 69.07 (s); 66.46 (s); 58.49 (s); 52.60 (s); 51.19 (d); 26.1 (d); 24.53 (d); 23.56 (d); 15.17 (s).

31P{1H} (CDCl3): δ(ppm)=−31.7.

EXAMPLE 2

Synthesis of bis[(dimethoxyethylphosphino)ethyl]ethoxyethylamine (PNP7)

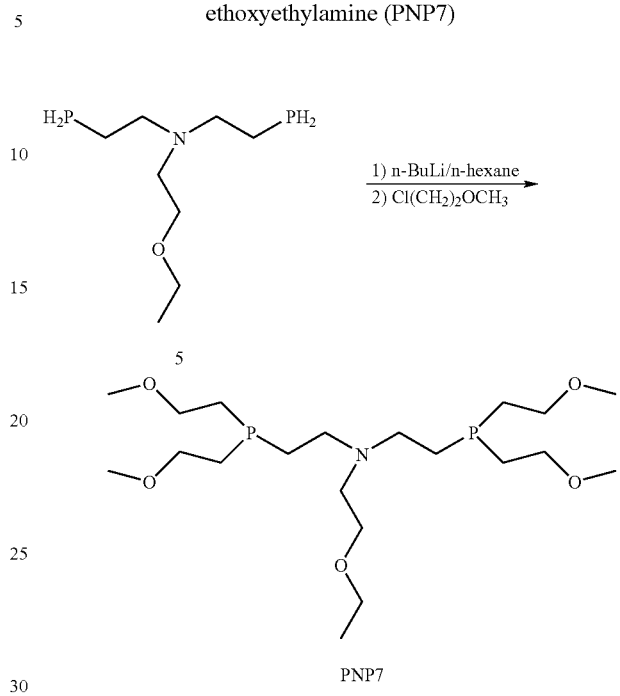

PNP7

A slight excess of n-BuLi (2.5 M in n-hexane; 1.61 mL, ca. 5% excess with respect to the stoichiometric amount corresponding to 1.53 mL, 3.84 mmol) was added via cannula through a rubber septum to a flask containing N,N-bis(2-phosphinoethyl)ethoxyethylamine (5) (200 mg, 0.96 mmol) in freshly distilled THF (10 mL). The solution became yellow-green coloured. The flask was cooled to 0° C. with an ice bath and, under stirring, 2-chloroethyl methylether (379 mg, 4.02 mmol) was added dropwise.

The mixture was left to reach room temperature. The mixture was then reduced to one third of the initial volume by a gentle stream of dinitrogen. The flask was cooled again with an ice bath and degassed water (5 mL) was added dropwise. Two phases were formed: the upper organic phase was grey-green coloured, whereas the aqueous phase was almost colourless. Degassed diethylether (20 mL) was added and the mixture was transferred in a separatory funnel (previously fluxed with dinitrogen) via cannula to avoid the contact with the atmosphere. Always under a dinitrogen atmosphere the lower aqueous phase was recovered in another separatory funnel and treated with additional diethylether (20 mL). Then the aqueous phase was discharged and the combined ethereal phases were placed in a 100 mL round bottom flask containing anhydrous Na2SO4 (ca. 500 mg). The solid was filtered off and washed with additional anhydrous diethylether (2×10 ml). The combined ethereal phases were concentrated under dinitrogen and then under vacuum (yield ca. 50%).

1H NMR (CDCl3): δ(ppm)=3.57-3.47 (12H); 3.33 (s, 12H); 2.66 (m, 6H); 1.77 (t, 8H); 1.64 (m, 4H); 1.20 (t, 3H).

13C NMR (CDCl3): δ(ppm)=70.37 (d); 69.01 (s); 66.51 (s); 58.50 (s); 52.60 (s); 50.94 (d); 27.87 (d); 24.73 (d); 15.18 (s).

31P{1H} (CDCl3): δ(ppm)=−39.1.

As clear from Example 1 as mentioned above, the bisphosphinoamine compound was prepared from diethyl(2-bromoethyl)phosphonate by four steps according to the method of the present invention.

EXAMPLE 3

Synthesis of bis[(dimethoxyethylphosphino)ethyl]methoxyethylamine (PNP10)

(i) Synthesis of N-(diethyl 2-phosphono)ethyl ethoxyethylamine (2')

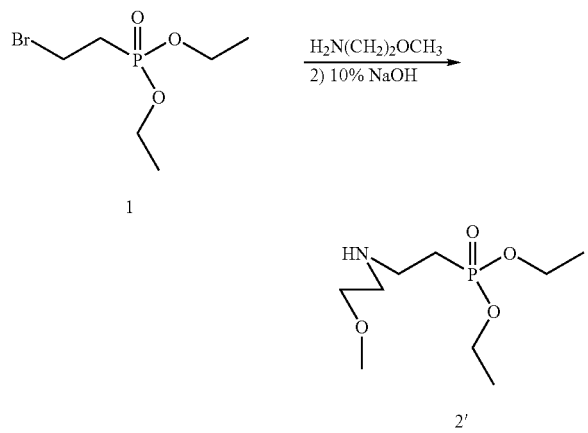

In a 25 ml two-necked round bottom flask was placed diethyl (2-bromoethyl)phosphonate (1) (2.45 g, 0.01 mol). Water (2 ml) and 2-methoxyethylamine (6 ml, 0.07 mol) were added. Additional water (4 ml) was added and the mixture was refluxed for 3 hours. After cooling the mixture was colourless and viscous. NaOH 10% (5 ml) was added and then the mixture was reduced in volume by roto-evaporation to remove the excess of unreacted amine and water. The viscous residue was treated with diethylether (3×30 ml) under vigorous stirring. The combined ethereal phases were treated with Na$_2$SO$_4$ (ca. 500 mg), filtered and concentrated by a gentle nitrogen stream and the residue dried under vacuum pump (yield 55%).

1H NMR (CDCl3): δ(ppm)=4.09 (m, 4H), 3.48 (t, 2H), 3.34 (s, 3H), 2.92 (m, 2H), 2.79 (t, 2H), 1.99 (m, 2H), 1.31 (t, 6H).

31P{1H} (CDCl3): δ(ppm)=31.1.

(ii) Synthesis of diethyl vinylphosphonate (3)

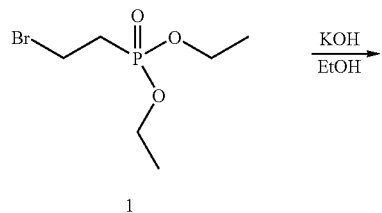

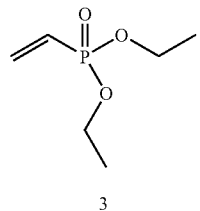

A 150 ml two-necked round bottom flask was filled with EtOH (85 ml). KOH pellets (2.52 g, 0.045 mol) were added. The mixture was stirred in an ice bath until complete KOH dissolution. Diethyl (2-bromoethyl)phosphonate (1) (8.1 ml, 0.045 mol) was added dropwise (30 minutes) by means of an equalizing pressure funnel. Meanwhile a white solid formed. The mixture was refluxed for 15 minutes, and, after cooling, was filtered using a frit. The white solid was washed with absolute EtOH and the filtrate was roto-evaporated, and finally dried under a vacuum pump for 15 minutes. The residue was distilled with a micro-distillator. The first fraction (43° C., 0.5 mmHg) corresponded to pure diethyl vinylphosphonate (3) (yield 90%).

1H NMR (CDCl3): δ(ppm)=5.99-6.36 (3H), 4.09 (m, 4H), 1.33 (t, 6H).

31P{1H} (CDCl3): δ(ppm)=18.1.

(iii) Synthesis of N,N-bis[(diethyl 2-phosphono)ethyl]methoxyethylamine (4')

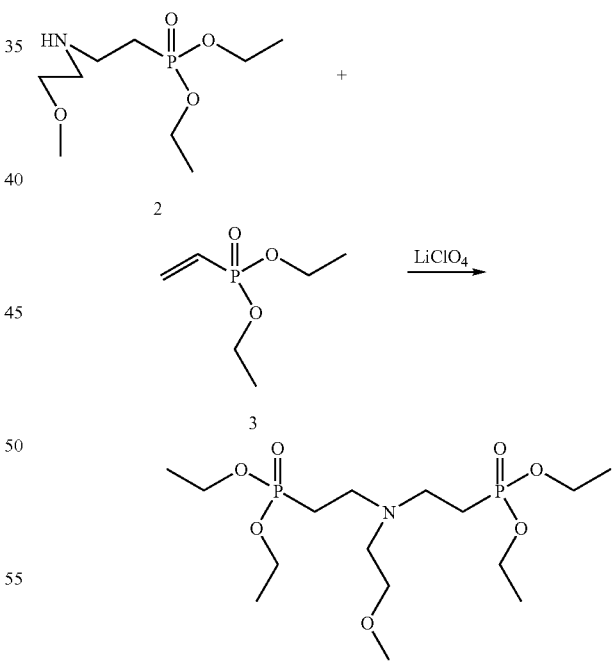

In a 2 ml vial N-(diethyl 2-phosphono)ethyl ethoxyethylamine (2') (148.3 mg, 0.625 mmol), diethyl vinylphosphonate (3) (66.5 mg, 0.625 mmol) and LiClO4 (66.5 mg, 0.625 mg) were added. The vial was degassed with dinitrogen, and then quickly and tightly closed. The vial was deepen for 7 hours at 75° C. in an oil bath. The resulting yellow oil was then treated with CHCl3 (3×2 ml) and extracted with H2O (6 mL) in a separator funnel. The lower organic layer was recovered while the water phase was treated again with CHCl3 (3 mL). The combined organic phases were evaporated with a N2 flow giving an oily residue. The excess of compound 3 was eliminated under vacuum (2 h, 10-2 tor). Yield 89%.

1H NMR (CDCl3): δ(ppm)=4.09 (m, 8H); 3.45 (t, 2H); 3.34 (s, 3H); 2.83°(m, 4H); 2.65 (t, 2H); 1.93 (m, 4H); 1.33 (t, 12H).

31P{1H} (CDCl3): δ(ppm)=31.3.

(iv) Synthesis of N,N-bis(2-phosphinoethyl)methoxyethylamine (5')

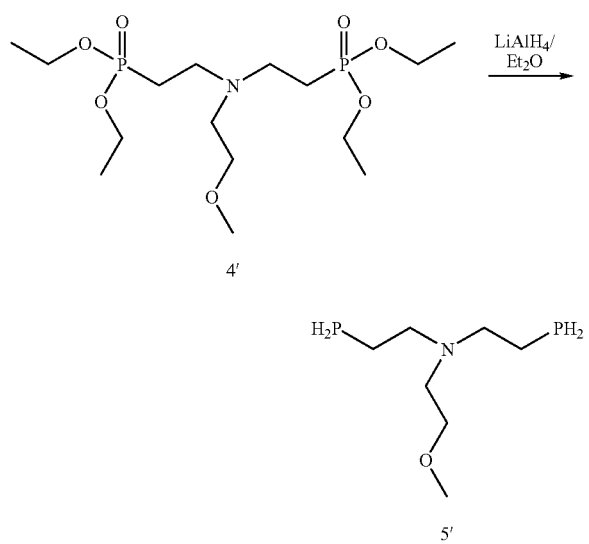

All the following manipulations were performed under N2. All solvent were previously degassed.

N,N-bis[(diethyl 2-phosphono)ethyl]methoxyethylamine (4') (533 mg, 1.32 mmol) was placed in a oven dried two-neck flask (50 ml) and freshly distilled anhydrous diethylether (5 mL) was added. The flask was cooled to 0° C. in an ice bath and LiAlH4 (1M in Et2O solution; 8 mL, 8 mmol) was added slowly in 3 minutes through a rubber septum with a syringe. The ice bath was removed and the mixture was left to stir at room temperature for 45 minutes. At the end the solution was white and cloudy. The flask was then cooled again to 0° C. (ice bath) and a degassed saturated water solution of Na2SO4 (5 mL) was carefully added (if necessary other Et2O aliquots (5 mL each) were added to maintain a constant volume). Anhydrous Na2SO4 was added (c.a. 400 mg) in order to eliminate all the amount of water. After 15 min, the solid was separated by filtration on a G2 frit. The filtrate was collected in a pre-weighted two-neck flask (50 ml). The ethereal solution was evaporated with a N2 flow followed by sucking in vacuum pump (30 min at 10-2 torr). Yield 88%.

1H NMR (CDCl3): δ(ppm)=3.46 (t, 2H); 3.35 (s, 3H) 2.93 (t, 2H); 2.28 (t, 2H); 2.67 (m, 6H); 1.63 (m, 4H).

31P{1H} (CDCl3): δ(ppm)=144.6.

(v) Synthesis of bis[(dimethoxyethylphosphino) ethyl]methoxyethylamine (PNP10)

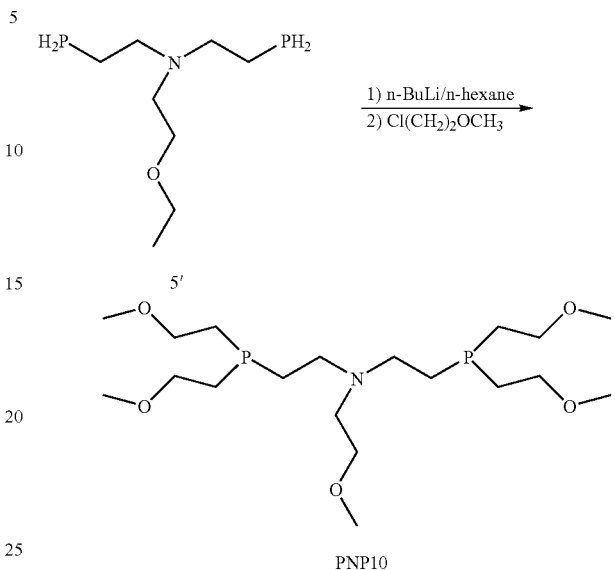

An excess of n-BuLi (2.5 M in n-hexane; 1.0 mL, correct stoichiometric amount corresponding to 0.50 mL, 1.24 mmol) was added via cannula through a rubber septum to a flask containing N,N-bis(2-phosphinoethyl)methoxyethylamine (5') (60 mg, 0.31 mmol) in freshly distilled THF (10 mL) at 0° C. The solution became dark (black-violet coloured). Still at 0° C., under stirring, 2-chloroethyl methylether (236 mg, 2.48 mmol) dissolved in distilled THF (5 mL) was added dropwise. The mixture was left to reach room temperature overnight becoming yellow-gold coloured. It was then reduced to one third of the initial volume by a gentle stream of dinitrogen. Distilled diethylether (20 mL) was added. The flask was cooled again with an ice bath and degassed water (5 mL) was added dropwise. Two phases were formed: the upper organic phase was yellow-gold coloured, whereas the aqueous phase was almost colourless. Degassed diethylether (20 mL) was added, and the mixture was transferred in a separatory funnel (previously fluxed with dinitrogen) via cannula to avoid the contact with the atmosphere. Always under a dinitrogen atmosphere the lower aqueous phase was recovered in another separatory funnel and treated with additional diethylether (2×10 mL). Then the aqueous phase was discharged and the combined ethereal phases were placed in a 100 mL round bottom flask containing anhydrous Na2SO4 (ca. 500 mg). The solid was filtered off under dinitrogen and washed with additional anhydrous diethylether (2×10 ml). The combined ethereal phases were concentrated under dinitrogen and then under vacuum (yield ca. 60%).

1H NMR (CDCl3): δ(ppm)=3.57-3.47 (10H); 3.33 (s, 12H); 3.32 (s, 3H); 2.66 (m, 6H); 1.78 (t, 8H); 1.65 (m, 4H).

13C NMR (CDCl3): δ(ppm)=71.02 (s); 70.39 (d); 58.86 (s); 52.48 (s); 52.52 (s); 50.83 (d); 27.96 (d); 24.75 (d).

31P{1H} (CDCl3): δ(ppm)=−39.0.

EXAMPLE 4

Preparation of $^{99m}$TcN-PNP5-DBODC

The technetium nitride complex of $^{99m}$TcN-PNP5-DBODC was prepared in Example 4. Herein, PNP5 and DBODC indicate as follows:

PNP5: bis(dimethoxypropylphosphinoethyl)ethoxyethyfamine

DBODC: diethoxyethyldithiocarbamate

An anhydrous stannous chloride (0.1 mg, Nakaraitesuk Lot. VIP5014), recrystallized succinic hydrazide (SDH) (1 mg, Ardrich Lot. 00229EQ) and dissodium ethylenediaminetetraacetate (1 mg, Dojin Kagaku, Lot. KKO78) dihydrate were dissolved in physiological saline (0.1 mL). To the solution, a solution of pertechnetium-99m acid ($^{99m}TcO_4^-$) (0.85 mL, 651 MBq/mL) was added and allowed to stand at a room temperature for 15 minutes. The resulting solution was adjusted to pH about 6.5 by adding 20 μL of an aqueous solution of sodium hydroxide (0.1 mol/L). Thus, $^{99m}TcN$ intermediate solution was obtained.

To the intermediate solution were added 0.5 mL of a solution of (4 mg/mL) (containing γ-cyclodextrine (Wako, Lot. LDK1242) at the concentration of 4 mg/mL as a solubilizer) and 0.5 mL of a solution of DBODC (4 mg/mL). Further, the resulting solution was adjusted to pH about 9 by the addition of 20 μL of an aqueous solution of sodium hydroxide (0.1 mol/L). Then, the adjusted solution was heated at a temperature of 100° C. for 15 minutes to obtain a solution of $^{99m}TcN$-PNP5-DBODC.

For the obtained solution of $^{99m}TcN$-PNP5-DBODC, TLC analysis was conducted according to the conditions as mentioned below to determine a radiochemical purity by the measurement of peak area %. As a result, the solutions of $^{99m}TcN$-PNP5-DBODC exhibited 92.1% purity.

TLC conditions:
TLC plate: Silica gel 60 (Merck)
Development phase: ethanol/chloroform/toluene/0.5M ammonium acetate=5/3/3/0.5
Development length: 10 cm
Detector: Radiochlomatoglamschana (Aroka, PS-201 type)

EXAMPLE 5

Preparation of $^{99m}TcN$-PNP7-DBODC and $^{99m}TcN$-PNP10-DBODC

The technetium nitride complexes of $^{99m}TcN$-PNP7-DBODC and $^{99m}TcN$-PNP10-DBODC were prepared in Example 5. Herein, PNP7 and PNP10 indicate as follows PNP7: bis(dimethoxyethylphosphinoethyl)ethoxyethylamine PNP10: bis(dimethoxyethylphosphinoethyl)methoxyethylamine An anhydrous stannous chloride (0.1 mg, Nakaraitesuk Lot. VIP5014), citric acid hydrazide (SDH) (1 mg, Tokyo Kasei) and disodium ethylenediaminetetraacetate (1 mg, Dojin Kagaku, Lot. KKO78) dihydrate were dissolved in physiological saline (0.1 mL). To the solution, a solution of pertechnetium-99m acid ($^{99m}TcO_4^-$) (1.5 mL, 3460 MBq/mL in the case of PNP7 and 3778 MBq/mL in the case of PNP10) was added and allowed to stand at a room temperature for 15 minutes. The resulting solution was adjusted to pH about 6.5 by adding 20 μL of an aqueous solution of sodium hydroxide (0.1 mol/L). Thus, $^{99m}TcN$ intermediate solution was obtained.

To the intermediate solution were added 0.5 mL of a solution of PNP7 or PNP10 (1 mg/mL) (containing γ-cyclodextrine (Wako, Lot. LDK1242) at the concentration of 4 mg/mL as a solubilizer) and 0.1 mL of a solution of DBODC (4 mg/mL). Further, the resulting solution was adjusted to pH about 9 by the addition of 30 μL of an aqueous solution of sodium hydroxide (0.1 mol/L). Then, the adjusted solution was heated at a temperature of 100° C. for 15 minutes to obtain a solution of $^{99m}TcN$-PNP7-DBODC or $^{99m}TcN$-PNP10-DBODC.

The obtained solution was subjected to HPLC under conditions as mentioned below to purify and recover $^{99m}TcN$-PNP7-DBODC or $^{99m}TcN$-PNP10-DBODC.

HPLC Conditions:
Column: Beckman Ultrasphere ODS 4.6 mm×25 cm+Guard Column 4.6 mm×4.5 cm
Mobile phase: 80% MeOH/20% 0.02 MPB (pH7.4)
Flow rate: 1.0 mL/min
Detector: RI Detector (Steffi), Urtraviolet absorptiometry The retention times (RT) of $^{99m}TcN$-PNP7-DBODC and $^{99m}TcN$-PNP10-DBODC were 14.5 and 11.7 minutes, respectively. The fractionated solutions were evaporated and dried under argon atmosphere. To the resulting residue was added an aqueous solution of EtOH (10%).

For the finally obtained solution of $^{99m}TcN$-PNP7-DBODC or $^{99m}TcN$-PNP10-DBODC, TLC analysis was conducted according to the conditions as mentioned below to determine a radiochemical purity by the measurement of peak area %. As a result, the solutions of $^{99m}TcN$-PNP7-DBODC and $^{99m}TcN$-PNP10-DBODC exhibited 92.7% and 91.0% purities, respectively.

TLC Conditions:
TLC plate: Silica gel 60 (Merck)
Development phase: ethanol/chloroform/toluene/0.5M ammonium acetate=5/3/3/0.5
Development length: 10 cm
Detector: Radiochromatogramschana (Aroka, PS-201 type)

EXAMPLE 6

Biodistribution of Technetium Nitride Complexes

The biodistribution of the technetium nitride complexes obtained in Examples 4 and 5 was evaluated when those complexes were administered into rats.

Sprague-Dawley rats (SD rats, females, 10 weeks aged) were anesthetized with intraperitoneal injections of ketamine (80 mg/kg) and xilazine (19 mg/kg). After forty five minutes, rats were anesthetized, each of $^{99m}TcN$-PNP5-DBODC, $^{99m}TcN$-PNP7-DBODC and $^{99m}TcN$-PNP10-DBODC was administered into the tail vein of the rats at a radioactive concentration of 140 to 180 MBq/mL. Two minutes and sixty minutes after the administration, the blood was recovered from the abdominal aorta of the rats. Then, the rats were killed painlessly, and organs were removed from the rats. The removed organs were weighted and measured for the radioactivity by a single channel analyzer (Applied Optical Research Industry Incorporated, 701-IC type). From the thus obtained values of the radioactivities, an accumulated rate (% ID/g) of the technetium nitride complex in each organs was calculated using an equation as follows:

Accumulated rate (% ID/g) for each organs=(Radioactivity of each organs (cpm)−Background (cpm))/(Total of radioactivity of each organs (values corrected on times)×Weight of each organs (g))×100

Further, based on the obtained accumulated rates, ratios of heart/lungs and heart/liver were also obtained.

In the above experiments, the measurements were repeated three or four times.

The obtained results are shown on Table 1.

TABLE 1

Radiodistribution of Complexes

| Accumulated rate (% ID/g) Time (min.) | N | Heart 2 | Heart 60 | Lungs 2 | Lungs 60 | Liver 2 | Liver 60 | Blood 2 | Blood 60 | Heart/lungs 2 | Heart/lungs 60 | Heart/liver 2 | Heart/liver 60 |
|---|---|---|---|---|---|---|---|---|---|---|---|---|---|
| TcN-PNP10-DBODC | 3 | 3.45 ± 0.31 | 3.33 ± 0.13 | 1.25 ± 0.13 | 0.54 ± 0.02 | 2.14 ± 0.12 | 0.18 ± 0.03 | 0.35 ± 0.06 | 0.01 ± 0.00 | 2.76 | 6.17 | 1.61 | 18.50 |
| TcN-PNP7-DBODC | 3 | 3.12 ± 0.39 | 3.31 ± 0.12 | 1.48 ± 0.24 | 0.63 ± 0.15 | 2.58 ± 0.36 | 0.18 ± 0.01 | 0.29 ± 0.04 | 0.01 ± 0.00 | 2.11 | 5.25 | 1.21 | 18.39 |
| TcN-PNP5-DBODC | 4 | 3.53 ± 0.20 | 2.98 ± 0.20 | 1.22 ± 0.15 | 0.32 ± 0.04 | 2.25 ± 0.58 | 0.14 ± 0.05 | 0.10 ± 0.02 | 0.00 ± 0.01 | 2.89 | 9.31 | 1.57 | 21.29 |

As seen from the results in Table 1, sixty minutes after the administration of the complexes, the clearances of all of the complexes were observed for all of the organs except for heart. Thus, the ratios of heart/lungs and heart/liver were excellent, and it was revealed that the complexes prepared by the method of the present invention can be markedly accumulated in heart, and hence is extremely useful for radiodiagnostic imaging.

Industrial Applicability

The method of the present invention enables the industrially advantageous and effective preparation of an intermediate compound, namely a bisphosphonoamine compound, which is used for preparing a technetium nitride complex for radiodiagnostic imaging. Thus, according to the method of the present invention, the technetium nitride complex can be prepared advantageously and effectively.

The invention claimed is:

1. A method for preparing a bisphosphonoamine compound represented by the following formula (I):

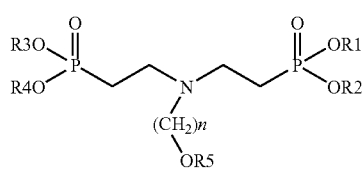

wherein R1, R2, R3, R4 and R5 are independently an alkyl group having 1 to 6 carbon atoms, and n is an integer of 1 to 6, which comprises the step of:

reacting a vinylphosphono compound of the following formula (II):

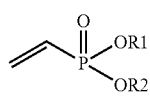

wherein R1 and R2 are as defined above, with a phosphonoamine compound of the following formula (III):

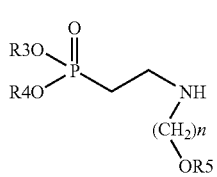

wherein R3, R4, R5 and n are as defined above, in the presence of a catalyst for condensation reaction.

2. The method according to claim 1, wherein the catalyst for condensation reaction is lithium perchlorate.

3. The method according to claim 1, wherein R1, R2, R3 and R4 are the same as each other.

4. The method according to claim 1, wherein R1, R2, R3 and R4 are methyl, ethyl, n-propyl or iso-propyl.

5. The method according to claim 1, wherein R5 is methyl, ethyl, n-propyl or iso-propyl.

* * * * *